(12) United States Patent
Musty et al.

(10) Patent No.: US 8,481,085 B2
(45) Date of Patent: Jul. 9, 2013

(54) PHARMACEUTICAL COMPOSITIONS COMPRISING CANNABIGEROL

(75) Inventors: Richard Musty, Burlington, VT (US); Richard Deyo, Winona, MN (US)

(73) Assignee: GW Pharma Limited, Salisbury (GB)

( * ) Notice: Subject to any disclaimer, the term of this patent is extended or adjusted under 35 U.S.C. 154(b) by 0 days.

(21) Appl. No.: 11/760,364

(22) Filed: Jun. 8, 2007

(65) Prior Publication Data

US 2008/0031977 A1 Feb. 7, 2008

Related U.S. Application Data

(60) Provisional application No. 60/813,814, filed on Jun. 15, 2006.

(51) Int. Cl.
*A01N 65/00* (2009.01)

(52) U.S. Cl.
USPC ......................................................... 424/725

(58) Field of Classification Search
None
See application file for complete search history.

(56) References Cited

U.S. PATENT DOCUMENTS

| | | | |
|---|---|---|---|
| 2006/0153941 A1 | 7/2006 | Musty et al. | |
| 2006/0257463 A1* | 11/2006 | Elsohly et al. | 424/449 |

FOREIGN PATENT DOCUMENTS

| | | |
|---|---|---|
| WO | WO 03/037306 A2 | 5/2003 |
| WO | WO 2004/026857 A2 | 4/2004 |
| WO | WO 2005/000830 A1 | 1/2005 |

OTHER PUBLICATIONS

Mechoulam, British Journal of Pharmacology, 2005, 146, 913-915.*
Pertwee, R.G. et al., "Evidence that (−)-7-hdroxy-4'-dimethylheptyl-cannabidiol activates a non-$CB_1$, non-$CB_2$, non-TRPV1 target in the mouse vas deferens," *Neuropharmacology* 2005; 48:1139-1146.
The United Kingdom Parliament, Select Committee on Science and Technology Ninth Report (1998) at http://www.parliament.the-stationery-office.co.uk/pa/ld199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.
Hillig, K. W . et al., "A Chemotaxonomic Analysis of Cannabinoid Variation in *Cannabis* (Cannabaceae)," *American Journal of Botany* 2004; 91(6):966-975.
Steru, Lucien et al., "The tail suspension test: A new method for screening antidpressants in mice", *Psychopharmacology* (1985) 85: 367-370.
Gut et al., Depression. The medicinal uses of cannabis and cannabinoids. Pharmaceutical Press $1^{st}$ ed. Jun. 17, 2004. p. 177.

* cited by examiner

*Primary Examiner* — Michael Meller
(74) *Attorney, Agent, or Firm* — Wolf, Greenfield & Sacks, P.C.

(57) ABSTRACT

The present invention relates to the use of cannabigerol (CBG) type compounds and derivatives thereof in the treatment of mood disorders.

1 Claim, 2 Drawing Sheets

Structure of Cannabigerol

Biosynthetic pathway of the major cannabinoids

PHARMACEUTICAL COMPOSITIONS COMPRISING CANNABIGEROL

RELATED APPLICATIONS

This application claims the benefit under 35 U.S.C. §119 (e) of U.S. provisional application 60/813,814, filed Jun. 15, 2006, the entire disclosure of which is incorporated herein by reference.

FIELD OF THE INVENTION

The present invention relates to the use of cannabigerol (CBG) type compounds and derivatives thereof in the treatment of mood disorders.

BACKGROUND OF THE INVENTION

Mood disorders are generally classified by type and include, but are not limited to:

A morbid or clinical depression, which is usually diagnosed when sadness or elation is overly intense and continues beyond the expected impact of an event. Symptoms often recur on an episodic basis or pursue a low-grade intermittent chronicity, which impairs the functioning of the sufferer.

Bipolar mood disorder, which commonly begins with depression and is characterised by periods of elation during the course of the illness.

Unipolar mood disorder, which is characterised as syndromal depression of episodes that last for typically 6 to 9 months.

The pharmaceuticals used in the treatment of Bipolar mood disorders can be grouped into three classes; the heterocyclic antidepressants (HCAs), monoamine oxidase inhibitors (MAOIs) and lithium salts.

HCAs are the largest class of antidepressants and include tricyclic antidepressants such as imipramine. The HCAs have no immediate effect on euphoria and therefore have a low abuse potential. This group of antidepressants work by increasing the availability of the biogenic amines norepinephrine and/or serotonin (5-HT) by blocking reuptake in the synaptic cleft. The side effects of HCAs include tachycardia, postural hypotension and cardio-toxicity. HCAs are also commonly associated with blurred vision, xerostomia, constipation, urinary hesitation, sedation and weight gain. The hypotensive side effects of HCAs often make them unsuitable for patients with mental disorders and the elderly.

MAOIs such as phenelzine are often prescribed for panic disorders. They work by the inhibition of the oxidative deamination of the 3 classes of biogenic amines; noradrenergic, dopaminergic and 5-HT. MAOIs are underused because of clinician's fears of hypertension that may result from dietary or drug reactions, popularly known as the 'cheese reaction' due to the high tyramine content in cheeses and other foods. Other common side effects of MAOIs include erectile difficulties, anxiety, nausea, dizziness, insomnia, edema and weight gain.

Lithium is used to stabilise the often unpredictable mood swings in bipolar mood disorder. The precise mechanism of action is unknown, but it is postulated that it is able to cause hyperpolarisation of the neuronal membrane. The most common acute benign side effects are tremour, fasciculation, nausea, diarrhoea, polyuria, polydipsia and weight gain. Lithium toxicity is more likely in elderly patients.

The applicants have previously shown that the cannabinoid cannabichromene is useful in the treatment of mood disorders as described in the International patent application WO2005/000830. However the actions of many cannabinoids such as THC are linked with an increase in mood disorders in users.

SUMMARY OF THE INVENTION

Surprisingly the applicants have found that cannabigerol (CBG) and cannabigerol type compounds (including cannabigerol propyl analogue (CBGV)) and derivatives thereof, are useful in the treatment of mood disorders, particularly depression.

The naturally occurring cannabinoid CBG is a precursor to the major cannabinoids CBD, CBC and THC and as such is rarely found in cannabis plants in any significant concentration. As such this cannabinoid was not thought to possess pharmacological properties.

According to the first aspect of the present invention there is provided a method of treating a mood disorder in a human patient which comprises administering to a patient in need thereof a therapeutically effective amount of at least one cannabigerol type compound or derivative.

Preferably the mood disorder to be treated is one or more of the following; morbid or clinical depression; unipolar mood disorder; bipolar mood disorder; syndromal depression; panic disorder and anxiety.

Preferably the mood disorder to be treated is depression.

References to CBG, CBG type compounds or derivatives thereof, particularly with regard to therapeutic use, will be understood to also encompass pharmaceutically acceptable salts of such compounds. The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

Cannabinoid biosynthesis begins when a precursor molecule reacts with geranylpyrophosphate to form a ringed structure. As shown in FIG. 1, CBG type compounds are mostly 21 carbon compounds.

Variation in the length of the side chain that is attached to the aromatic ring (bottom right hand side of the structure) can produce different types of CBG compounds. For example when the side chain is a pentyl (5 carbon) chain the compound produced will be CBG. If the pentyl chain is replaced with a propyl (3 carbon) chain the CBD type compound formed is CBGV (cannabigeroldivarin). The propyl variant will be formed if a 10 carbon precursor is reacted at the first stage of the biosynthetic pathway rather than a 12 carbon compound.

Synthetic variants of CBG include dimethylheptyl CBG. This variant also has variations in the side chain of the CBG compound.

The scope of the invention also extends to derivatives of CBG that retain the desired activity of being useful in the treatment of mood disorders. Derivatives that retain substantially the same activity as the starting material, or more preferably exhibit improved activity, may be produced according to standard principles of medicinal chemistry, which are well known in the art. Such derivatives may exhibit a lesser degree of activity than the starting material, so long as they retain sufficient activity to be therapeutically effective. Derivatives may exhibit improvements in other properties that are desirable in pharmaceutical active agents such as, for example, improved solubility, reduced toxicity, enhanced uptake, etc.

Preferably the at least one cannabigerol type compound or derivative thereof is an extract from a cannabis plant.

The term "cannabis plant/s" encompasses wild type *Cannabis sativa* and also variants thereof, including cannabis chemovars (varieties characterised by virtue of their chemical composition) which naturally contain different amounts of the individual cannabinoids, also *Cannabis sativa* subspecies *indica* including the variants var. *indica* and var. *kafiristanica*, *Cannabis indica* and also plants which are the result of genetic crosses, self-crosses or hybrids thereof. The term "cannabis plant material" is to be interpreted accordingly as encompassing plant material to be derived from one or more cannabis plants. For the avoidance of doubt it is hereby stated that cannabis plant material includes herbal cannabis and dried cannabis biomass.

More preferably the extract from the cannabis plant comprises all of the naturally occurring cannabinoids and other non-cannabinoid components that are co-extracted with the at least one cannabigerol type compound or derivative thereof.

An extract from a cannabis plant contains in addition to one or more cannabinoids, one or more non-cannabinoid components which are co-extracted with the cannabinoids from the plant material. Their respective ranges will vary according to the starting plant material and the extraction methodology used. Cannabis plant extracts may be obtained by various means of extraction of cannabis plant material. Such means include but are not limited to: supercritical or subcritical extraction with $CO_2$, extraction with hot gas and extraction with solvents.

In one embodiment the extract from the cannabis plant may be enriched for cannabigerol. In other words the extract contains a greater proportion of the total cannabinoid content as cannabigerol as compared to the cannabinoid composition from which the extract was prepared.

This enrichment may be achieved by selecting a fraction of the initial plant extract or by purifying the plant extract further after extraction to select specifically for cannabigerol.

Preferably the cannabis plant extract included in the pharmaceutical formulation of the invention will contain greater than or equal to 80% (w/w) cannabigerol of the total cannabinoid content, more preferably greater than or equal to 90%, more preferably greater than or equal to 95%, more preferably still greater than or equal to 99%.

In a further embodiment the at least one cannabigerol type compound or derivative thereof is isolated or substantially pure.

Isolated or substantially pure cannabigerols will be substantially free of other cannabinoids and other non-cannabinoid components such as terpenes. The isolated or substantially pure cannabigerols may be of natural i.e. plant origin or they may be synthetically produced compounds.

The process disclosed in the applicants granted United Kingdom patent GB2393721 describes a process for preparing substantially pure CBG.

"Substantially pure" is defined herein as preparations of cannabigerol type compounds or derivatives thereof having a chromatographic purity of greater than 95%, preferably greater than 96%, more preferably greater than 97%, more preferably greater than 98%, more preferably greater than 99% and most preferably greater than 99.5%, as determined by area normalisation of an HPLC profile.

The pharmaceutical formulation of the invention may be formulated for delivery nasally, sublingually, buccally, topically, orally, rectally, intravenously, intra-peritoneally, intramuscularly, subcutaneously, transdermally, intra-vaginally, intra-urethrally, by nebuliser, as inhaled vapour or by instillation into the bladder.

The formulation may be in liquid or solid dosage form and may include in addition to the active, other pharmaceutically acceptable components such as excipients, solvents, diluents, fillers, salts, buffers, stabilisers, solubilisers etc. The dosage form may contain other pharmaceutically acceptable excipients for modifying conditions such as pH, osmolarity, taste, viscosity, sterility, lipophilicity, solubility etc. The choice of diluents, carriers or excipients will depend on the dosage form, which may in turn be dependent on the route of administration.

Solid dosage forms include for example, tablets, capsules, powders, dispersible granules, cachets and suppositories, including sustained release and delayed release formulations.

Liquid dosage forms include solutions, suspensions and emulsions.

Aerosol preparations suitable for inhalation may include solutions and solids in a powder form, which may be combined with a pharmaceutically acceptable carrier, such as an inert compressed gas.

Also encompassed are dosage forms for transdermal administration including creams, lotions, aerosols and or emulsions.

Pharmaceutical preparations may be conveniently prepared in a unit dosage form according to standard procedures of pharmaceutical formulation. The quantity of active compound per dosage form may be varied according to the nature of the active and the intended dosage regime. Generally this will be with in the range of 0.1 to 1000 mg.

In a second aspect of the present invention there is provided a method of treating a mood disorder in a human patient which comprises administering to a patient in need thereof a therapeutically effective amount of at least one cannabigerol type compound or derivative, wherein the pharmaceutical formulation further comprises one or more additional cannabinoids.

Preferably the one or more additional cannabinoid is cannabidiol (CBD).

Alternatively the one or more additional cannabinoid is cannabichromene (CBC).

DETAILED DESCRIPTION OF THE INVENTION

There are over sixty identified cannabinoids that are known to be produced the by cannabis plant. Of these cannabinoids there are eight different main classes of cannabinoids: cannabigerol-type; cannabichromene-type; cannabidiol-type; tetrahydrocannabinol-type; cannabielsoin-type; iso-tetrahydrocannabinol-type; cannabicyclol-type; and cannabicitran-type.

All of these main classes of cannabinoids are derived from cannabigerol-type compounds and differ mainly in the way the CBG precursor is cyclised.

The structure of cannabigerol is shown in FIG. 1 and the biosynthetic pathway is detailed in FIG. 2. Cannabinoid production in cannabis plants begins when an enzyme causes geranyl pyrophosphate and olivetolic acid to condense to form cannabigerol. The CBG cannabinoid is then usually converted by cannabinoid synthase enzymes to cannabidiol (CBD), cannabichromene (CBC) or tetrahydrocannabinol (THC).

Due to the nature of the biosynthetic pathway of cannabinoids most cannabis plants do not comprise a large amount of CBG. As such the pharmacology of CBG is largely unknown and it has been postulated that CBG is merely a precursor to other more pharmacologically active cannabinoids. The inventors postulated that it is possible, due to the biosynthetic pathway of the cannabinoids, that CBG will share some common properties with its products such as CBD and CBC. Also it is conceivable that the combination of CBG with its products such as CBC, CBD and THC will produce a greater and more beneficial effect than that produced by CBG alone.

It was shown by Elsohly et al. in 1992 that CBG had antimicrobial properties and more recently in 2005 Maor et al. described a synthetic analogue of CBG, CBG-dimethyl heptyl which possessed hypotensive and vasorelaxant properties. Compared with the vast knowledge available on THC or CBD, CBG's properties are relatively unknown.

Some patients have found cannabis to be useful in the treatment of anxiety, depression and bipolar mood disorders (Zimmerman, 1998). However reports on the therapeutic potential of cannabis are often contradictory as they describe the effects of whole, usually smoked cannabis, rather than the actions of the specific cannabinoids themselves. Indeed THC is often associated with anxiety and mood disorders, particularly in recreational users.

BRIEF DESCRIPTION OF THE DRAWINGS

Certain aspects of this invention are further described, by way of example only, with reference to the accompanying drawings in which.

Figure 1:
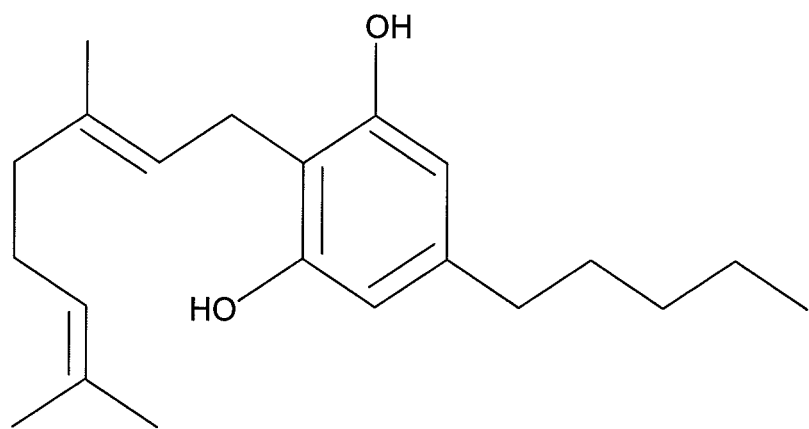
FIG. 1 shows the structure of cannabigerol.
Figure 2:
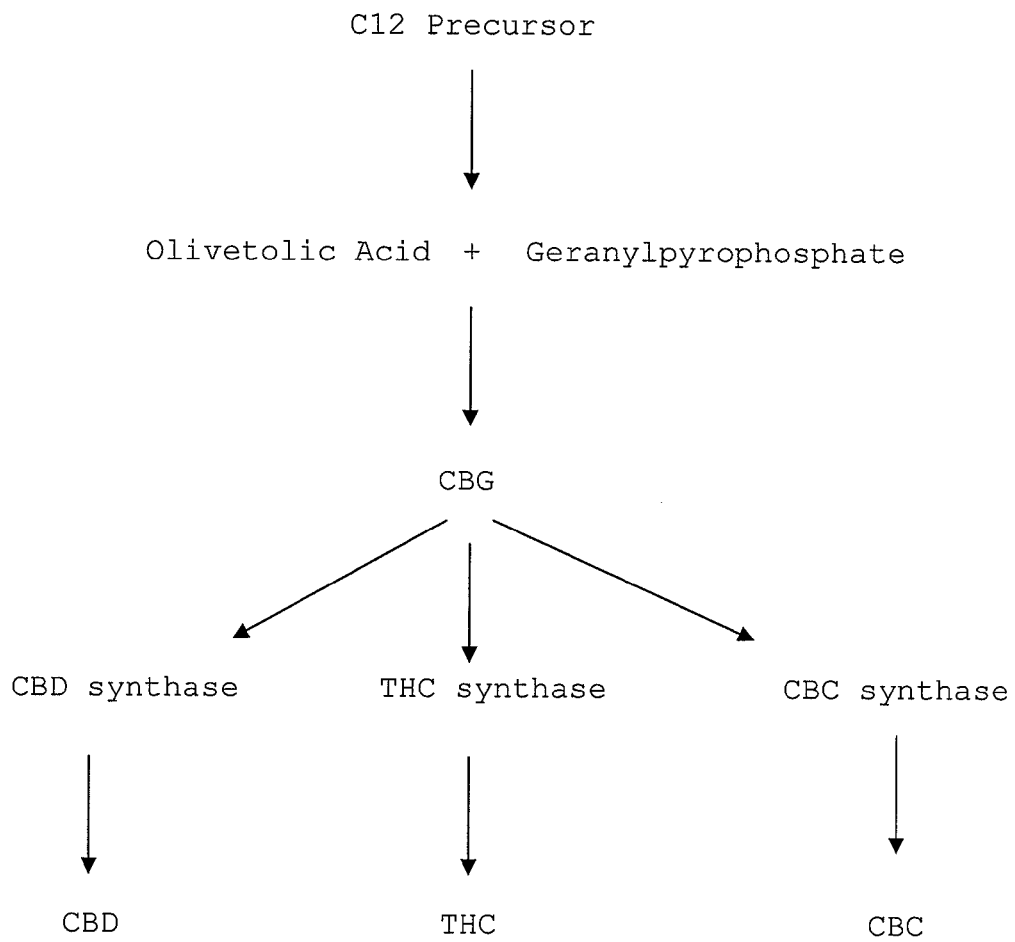
FIG. 2 shows the biosynthetic pathway of the major cannabinoids.

The present invention is further illustrated by the following Example, which in no way should be construed as further limiting. The entire contents of all of the references (including literature references, issued patents, published patent applications) cited throughout this application are hereby expressly incorporated by reference for the purpose cited herein.

EXAMPLE 1

Alteration of Behavioural Despair in an Animal Model of Depression

A substantially pure extract of cannabigerol, purified from a cannabis plant extract, was tested for its ability to modify the behaviour of mice during an open field test and a tail suspension test (Steru et al., 1985, Psychopharmacology (Berl.) 85(3), 367-370). The CBG extract was compared to a known antidepressant imipramine.

The experiment used groups of 7-8 C57 B16J mice and these were tested with doses of 0, 5, 10, 20, 40, 60 and 80 mg/kg ip of CBG extract. The dose of imipramine that was used was the standard dose that is known to produce an anti-depressant effect of 30 mg/kg ip. One group of animals were administered a vehicle control.

The open field apparatus consisted of a 44.5×44.5×30 cm chamber with clear plastic walls and a white plastic floor. Behaviours were recorded using a Quasar video recorder suspended above the chamber. The chamber was divided into four equal sized quadrants during scoring by placing a clear plastic template on the video screen. Behaviours were scored using data collection software.

The animals were subjected to a tail suspension test whereby a sound-attenuated chamber with a titanium bar mounted 15 cm from the floor was used. An opto-electronic sensor was mounted in a white plastic column and positioned from the mounting bar. An infra-red light transmitted from an LED onto the animal. If the animal moved, the amount of light collected by the phototransistor would increase or decrease depending on the size of the movement.

On the day of testing the mice were weighed and randomly assigned to a group prior to test article or control drug being injected intraperitoneally. Thirty minutes later each mouse was tested on the tail suspension test for six minutes.

The mouse was suspended from a bar by the tip of its tail using adhesive tape so that the tip of their nose was 2 cm from the floor of the chamber. The total number of movements and total amount of time spent immobile were recorded.

Immediately after the tail suspension test the mouse was placed individually in the open-field chamber for five minutes. The frequency of crossings, rears, grooming and defecation were recorded for each subject.

Results:

Antidepressant effects are indicated by an increase in the frequency of struggling activity during the test. In addition the degree or amplitude of struggling is thought to be a predictor of antidepressant activity.

At a dose of CBG greater than or equal to 40 mg/kg the amount of struggling was significantly increased compared with the animals administered the vehicle control. This dose of CBG gave similar responses as the standard dose of imipramine.

Conclusion:

The data presented suggest that CBG may induce antidepressant effects. Moderate doses of CBG produced behaviours that were consistent to imipramine in the tail suspension test and as such the use of this naturally occurring cannabinoid may have beneficial effects over that of HCA antidepressants such as imipramine which are known to cause many side effects in users.

The invention claimed is:

1. A method of treating a bipolar or unipolar mood disorder in a human in need thereof comprising administering to the human a therapeutically effective amount of isolated cannabigerol, wherein the isolated cannabigerol is administered as a unit dosage form that comprises the isolated cannabigerol in an amount of from 0.1 mg to 1000 mg, and wherein the isolated cannabigerol is not administered as an inhaled vapor.

* * * * *